(12) United States Patent
Melot et al.

(10) Patent No.: US 9,724,446 B2
(45) Date of Patent: Aug. 8, 2017

(54) METHOD FOR OBTAINING A COMPOSITE HEMOCOMPATIBLE MATERIAL AND RESULTING MATERIAL

(75) Inventors: Marion Melot, Issy les Moulineaux (FR); Antoine Capel, Pessac (FR)

(73) Assignee: CARMAT, Velizy Villacoublay (FR)

( * ) Notice: Subject to any disclaimer, the term of this patent is extended or adjusted under 35 U.S.C. 154(b) by 495 days.

(21) Appl. No.: 13/641,850

(22) PCT Filed: Apr. 6, 2011

(86) PCT No.: PCT/FR2011/050768
§ 371 (c)(1),
(2), (4) Date: Nov. 6, 2012

(87) PCT Pub. No.: WO2011/131887
PCT Pub. Date: Oct. 27, 2011

(65) Prior Publication Data
US 2013/0042957 A1    Feb. 21, 2013

(30) Foreign Application Priority Data

Apr. 22, 2010  (FR) .................................. 10 01724

(51) Int. Cl.
  B32B 37/12     (2006.01)
  A61L 15/40     (2006.01)
  A61L 27/18     (2006.01)
  A61L 27/36     (2006.01)

(52) U.S. Cl.
  CPC .............. *A61L 15/40* (2013.01); *A61L 27/18* (2013.01); *A61L 27/3691* (2013.01); *A61L 2430/40* (2013.01); *Y10T 156/10* (2015.01)

(58) Field of Classification Search
  CPC .............. A61F 2/2415; A61L 27/3604; A61L 27/3687; A61L 27/40
  USPC ......................................................... 156/60
  See application file for complete search history.

(56) References Cited

U.S. PATENT DOCUMENTS

| 5,135,539 | A | 8/1992 | Carpentier |
| 6,352,708 | B1 * | 3/2002 | Duran et al. ................... 424/423 |
| 6,986,735 | B2 * | 1/2006 | Abraham et al. ............... 600/36 |
| 7,214,344 | B2 * | 5/2007 | Carpentier et al. ............. 422/28 |
| 8,007,992 | B2 * | 8/2011 | Tian et al. ..................... 435/1.1 |
| 2001/0004715 | A1 * | 6/2001 | Duran et al. ................. 623/23.72 |
| 2005/0256588 | A1 * | 11/2005 | Sawa et al. .................. 623/23.72 |
| 2006/0253188 | A1 * | 11/2006 | Case ..................... A61F 2/2415 623/1.24 |
| 2008/0279910 | A1 * | 11/2008 | Capel et al. ................... 424/423 |

FOREIGN PATENT DOCUMENTS

| EP | 1 785 154 | 5/2007 |
| WO | 2004/003178 | 1/2004 |

OTHER PUBLICATIONS

B.D. Flockhart, The critical micelle concentration of sodium dodecyl sulfate in ethanol-water mixtures, Journal of Colloid Science, vol. 12, Issue 6, 1957, pp. 557-565, ISSN 0095-8522, http://dx.doi.org/10.1016/0095-8522(57)90061-2. (http://www.sciencedirect.com/science/article/pii/0095852257900612).*
International Search Report dated Jul. 12, 2011.
J. Ramshaw, et al., "Precipitation of Collagens by Polyethylene Glycols," XP000600477, Academic Press Inc., Feb. 17, 1984, pp. 361-365.

* cited by examiner

*Primary Examiner* — Matthew Daniels
*Assistant Examiner* — Marta Dulko
(74) *Attorney, Agent, or Firm* — Dickinson Wright

(57) ABSTRACT

The present invention relates to a method for manufacturing a hemocompatible material comprising a synthetic substrate and animal biological tissue, according to which said animal biological tissue is dehydrated and adhered to said synthetic substrate by means of a dispersion of the material forming said synthetic substrate. According to the invention, the animal biological tissue is only dehydrated chemically by immersing said animal biological tissue in a bath consisting of a solution containing at least 80 wt % of polyethylene glycol.

12 Claims, No Drawings

METHOD FOR OBTAINING A COMPOSITE HEMOCOMPATIBLE MATERIAL AND RESULTING MATERIAL

FIELD OF THE INVENTION

The present invention relates to a method for obtaining a composite hemocompatible material as well as such a material being obtained by implementation of such method.

BACKGROUND OF THE INVENTION

It is known that blood is a very sensitive liquid living tissue and that it is easily altered upon contact with chemical substances or upon an exposure to mechanical constraints, for example upon shearing; it coagulates upon a contact with most of the inert materials or upon stases. In reality, there are very few hemocompatible materials and most of them need anticoagulant taking by a patient bearing such a hemocompatible material.

It is known moreover that (see for example document U.S. Pat. No. 5,135,539) there exist cardiac prostheses wherein the artificial ventricles comprise flexible membranes of a hemocompatible material being operated by fluid impulses so as to activate blood. In such case, the hemocompatibility of said membranes is particularly critical, due to the fact that the membranes are mobile and in contact with a complex and often turbulent blood flow.

In the state of art, substantially hemocompatible materials are known, which are either synthetic or from biological origin.

Synthetic materials are generally elastomers of polyurethane or silicone; they are used either with a smooth surface, so as to reduce the platelet or blood adhesions, or with a porous surface, so as to allow the adhesion of a biological layer adapted to serve as an interface with blood. Such synthetic materials present good qualities of flexibility, imperviousness and deformability, but need the use of anticoagulants.

The materials of biological origin are animal tissues or are reconstituted from biological material, for instance collagen. Tissues of animal type must be chemically fixed (the most often with glutaraldehyde) when they aim to be implanted into the human body, so as to avoid immunological reactions. Such so-treated biological materials generally present excellent hemocompatible properties and do not need anyway the use of anticoagulants by the patient, but they are absolutely not impervious.

On the contrary, synthetic materials, so-called hemocompatible and implantable, generally have interesting mechanical and imperviousness characteristics, but are only tolerated in the blood flow with the help of a strict anticoagulation.

In order to be in a position to take advantage of the good mechanical and imperviousness properties of the synthetic materials and of the good hemocompatibility characteristics of the materials of biological origin, the document U.S. Pat. No. 5,135,539 provides a superposition of a synthetic material membrane and a biological origin membrane. However, such an arrangement leads to the formation of an intermediate chamber between said membranes, which can be the object of undesirable infections or liquid collections.

In order to remedy such disadvantages of the above mentioned state of the art, European patent EP 1,785,154 describes a hemocompatible material comprising a resistant, flexible and impervious synthetic material, for instance being made of an elastomer of polyurethane or silicone, and an animal biological tissue, for example, from animal pericardium, said biological tissue being made integral with said substrate through a dispersion of the constituent material of said substrate in a solvent, said constituent material impregnating said animal biological tissue.

Thus, thanks to the document EP 1,785,154, a composite material is obtained, the hemocompatibility of which is provided by the biological tissue, whereas the mechanical resistance and the imperviousness are brought by the synthetic substrate. It should moreover be noticed that, when said biological tissue consists in an animal pericardium, for example a bovine pericardium, said biological tissue is itself resistant and participates in the mechanical resistance of said composite material.

In order to allow the integration of said animal biological tissue onto said synthetic substrate through said dispersion, it is indispensable to dehydrate said animal biological tissue. To do so, the document EP 1,785,154 envisages to lyophilize said animal biological tissue, which not only dehydrates the latter, but also allows to hold the tridimensional structure of said biological tissue after dehydration. Indeed, when a biological tissue is dehydrated on ordinary conditions, the constituent collagen fibers come in contact with each other and irreversible chemical reactions occur, making the subsequent rehydration of the biological tissue impossible. On the contrary, lyophilizing allows the structure of the animal biological tissue to be immobilized by freezing, then the water to be removed at very low pressure by sublimation, thus with no possibility of moving or rearranging fibers. However, the period of the lyophilizing step is long (at least 96 hours) and it is necessary to implement a specific and costly infrastructure. Furthermore, The lyophilizing procedure is delicate, since dehydration must not be complete, otherwise the animal biological tissue would be irremediably damaged. Now, the dehydration efficiency depends on the thickness and the nature of said biological tissue, so that it is difficult to master and the lyophilizing step is inevitably accompanied with a quite high percentage of waste. Moreover, such incomplete dehydration of the animal biological tissue makes the latter instable, so that the storing and transport thereof on the lyophilized condition are complex and need to be put under vacuum.

The present invention aims at remedy such drawbacks.

SUMMARY OF THE INVENTION

For this purpose, according to the invention, the method for making a hemocompatible material comprising a resistant and impervious synthetic substrate and an animal biological tissue, chemically fixed so as to avoid immunological reactions, such a method wherein said animal tissue is dehydrated, said dehydrated animal biological tissue is glued on said synthetic substrate through a dispersion of the constituent material of said synthetic substrate in a solvent so that said constituent materiel impregnates said animal biological tissue and then said solvent is removed, is remarkable in that the dehydration is only obtained by a chemical way through the immersion of said animal biological tissue in a bath made of a solution of polyethylene glycol at at least 80% in weight.

Thus, said solution of polyethylene glycol at at least 80% in weight enables to obtain quickly (about 24 hours) an animal biological tissue membrane, which does not contain any water, which is indispensable for the gluing on the synthetic substrate, but which is perfectly re-hydratable with no alteration of said tissue and without any surface retraction. The polyethylene glycol acts as a mask in the tridimensional structure of the tissue, which can be thus stored at an ambient temperature of 20° C. (+/−2° C.), in a clean packaging being protected against dust. Moreover, the polyethylene glycol is easily rinsed, it is not toxic for the environment and for the operator and is biocompatible. Finally, the polyethylene glycol does not disturb in any way the penetration of the elastomer in dispersion into the biological tissue, upon the gluing operation.

It is to be noticed that, in the method of the document EP 1,785,154, it is provided that, to further improve the preservation of the tissue structure thereof upon lyophilizing, the animal biological tissue is previously treated during several days by polyethylene glycol. However, it should be noticed that such a treatment made during a long period and thus with a solution of polyethylene glycol in a low concentration (about 6% in weight of polyethylene glycol for 94% in weight of water) only aims at assisting in the preservation of the structure of the animal biological tissue upon lyophilizing and does not relate to the dehydration of the latter, such dehydration being totally obtained by the lyophilizing step.

Furthermore, it will be noticed that the article of RAMSHAW J. A. M. et al. "Precipitation of collagens by polyethylene glycols", Analytical Biochemistry, Academic Press Inc., New York, vol. 141, no. 2, 1, Sep. of 1984, pp. 361-365, XP000600467 relates to:
  the collagen and not an animal tissue;
  the precipitation of collagen in a liquid medium and not gluing on a support; and
  the precipitation of the collagen by polyethylene glycol and not the dehydration of an animal biological tissue by polyethylene glycol.

In no way, such article describes or suggests to replace, with the same results, the lyophilizing dehydration of an animal biological tissue by a dehydration of said animal biological tissue through an immersion in a bath made of a solution of polyethylene glycol at at least 80% in weight.

DETAILED DESCRIPTION OF THE INVENTION

To obtain the composite hemocompatible material according to the present invention, the following basic steps are implemented:

1. first, in a known manner, the animal biological tissue, preferably made of pericardium, is chemically fixed by any appropriate product, such as an aldehyde. In this last case, the glutaraldehyde is preferably used, for example with a concentration of 0.625%. Such a chemical fixation guarantees for the biological tissue an absence of antigenicity, a chemical stability, both biological and physical, and particularly a resistance to temperature variations and mechanical constraints.

2. Then, the animal biological tissue is dehydrated by a chemical way by immersion in a bath made of a solution of polyethylene glycol at at least 80% in weight. Said bath is advantageously an aqueous solution comprising at least 90% in weight of polyethylene glycol or an aqueous solution comprising at least 80% in weight of polyethylene glycol and 10% in weight of alcohol. Moreover, the polyethylene glycol being used to form said bath (formula HO—$CH_2$—($CH_2$—O—$CH_2$)$_n$—$CH_2$—OH) advantageously presents a molar mass comprised between 100 and 800.

The duration of the immersion of said animal biological tissue in said bath is about 24 hours and, during such immersion, it is advantageous that bath is submitted to a slight stirring and that the temperature thereof is at least equal to the room temperature (for example, about 37° C.)

At the end of the immersion, said animal biological tissue is taken out of said bath and the excess of the solution of polyethylene glycol impregnating said biological tissue is stanched.

3. Furthermore, on said flexible synthetic substrate, which is advantageously made of an elastomer of polyurethane or silicone, a layer of a dispersion of the constituent material of said substrate in a solvent is deposited. For example, if said substrate is a polyurethane elastomer, said dispersion contains biocompatible polyurethane in a solvent depending of the polyurethane, which can be dimethylacetamide. Such dispersion, which can be deposited on said substrate on any known way (coating, spraying, etc.) aims at serving as a hemocompatible adhesion agent with the biological tissue. Then, on said hemocompatible adhesion agent layer, said dehydrated biological tissue—which becomes impregnated with said dispersion—is applied to provide the mechanical adhesion of said biological tissue on said substrate and obtain said composite material;

4. afterwards, the removal of the solvent of said hemocompatible adhesion agent is made, for example, by a warm drying, warm drying under vacuum and/or by warm extraction in a physiological serum. Preferably, the elimination of the solvent is obtained by a slow warm extraction (for example, at about 40° C.) followed of an extraction under vacuum and completed by an extraction in a physiological serum.

5. Finally, the composite material is rehydrated with physiological serum.

In addition, to the basic steps 1 to 5 described hereinabove, the method according to the invention can comprise, after the step 2 of immersion of the animal biological tissue in said bath of polyethylene glycol and before the step 3 of adhesion of said animal biological tissue on said flexible synthetic substrate, one or two of two extra steps as follows:

6. drying of said animal biological tissue soaked with polyethylene glycol under a controlled atmosphere during several hours (for example 24 hours) and at a temperature at least equal to the room temperature (for example 37° C.)

7. application on the side of said animal biological tissue to be glued on said synthetic substrate, of a degreasing and drying volatile solvent, such as acetone or ether.

Furthermore, the step 5 of rehydration of the composite material can be implemented either immediately, of subsequently, after the step 4 of elimination of the solvent. If such rehydration is delayed after the step 4, said composite material can:
  be held on a dehydrated condition up to the use thereof and be rehydrated just before said use; or
  be held in a solution of polyethylene glycol, just like the solution of dehydration step 2 up to the use thereof, the rehydration of the step 5 being made just before said use.

Whatever the above mentioned conservation mode, said conservation can be improved by a sterilization step, for example with ethylene oxide or with gamma-beta rays.

The invention claimed is:

1. A method for making a hemocompatible material comprising a resistant and impervious synthetic substrate and an animal biological tissue, said method comprising the steps of:
  chemically fixing said animal biological tissue so as to avoid immunological reactions,
  chemically, dehydrating said fixed animal tissue without lyophilizing, and
  gluing said chemically dehydrated animal biological tissue onto said synthetic substrate through a dispersion of constituent material of said synthetic substrate in a solvent by impregnating said animal biological tissue with said constituent material and then removing said solvent, wherein the step of dehydrating said fixed animal tissue is a chemical dehydration obtained only by a chemical way through immersing said fixed animal biological tissue in a bath made of an aqueous solution of polyethylene glycol of at least 80% in weight, and said fixed animal biological tissue is immersed in said bath for about 24 hours, and wherein said bath is an aqueous solution comprising at least 80% in weight of polyethylene glycol and 10% in weight of alcohol.

2. The method according to claim 1,
wherein said bath is an aqueous solution comprising at least 90% in weight of polyethylene glycol.

3. The method according to claim 1,
wherein the polyethylene glycol of said solution presents a molar mass comprised between 100 and 800.

4. The method according to claim 1,
wherein said bath presents a temperature at least equal to the room temperature and is stirred during the immersion of said animal biological tissue.

5. The method according to claim 1,
wherein an excess of the solution of polyethylene glycol impregnating said animal biological tissue after immersion in said bath is stanched before gluing said animal biological tissue on said synthetic substrate.

6. The method according to claim 1,
wherein, after immersion in said bath and before gluing on said synthetic substrate, said animal biological tissue is dried during several hours at a temperature at least equal to the room temperature.

7. The method according to claim 1,
wherein after immersion in said bath and before gluing on said synthetic substrate, a volatile degreasing and drying solvent is applied on the side of said animal biological tissue directed towards said synthetic substrate.

8. The method according to claim 7,
wherein said degreasing and drying solvent is selected between acetone and ether.

9. The method according to claim 1,
wherein said hemocompatible material is rehydrated immediately after the removal of said solvent from the dispersion of the constituent material of the synthetic substrate.

10. The method according to claim 1,
wherein said hemocompatible materiel is rehydrated subsequently after the removal of said solvent from the dispersion of the constituent material of the synthetic substrate.

11. The method according to claim 10,
wherein, after the removal of said solvent from the dispersion of the constituent material of the synthetic substrate, said hemocompatible material is held on a dehydrated condition and is rehydrated just before the use thereof.

12. The method according to claim 10,
wherein, after the removal of said solvent from the dispersion of the constituent material of the synthetic substrate, said hemocompatible material is held in a solution of polyethylene glycol and is rehydrated just before the use thereof.

* * * * *